US012617742B2

(12) United States Patent
Dewilde et al.

(10) Patent No.: US 12,617,742 B2
(45) Date of Patent: May 5, 2026

(54) INTEGRATED PROCESS TO PRODUCE ALDEHYDES FROM SYNTHESIS GAS

(71) Applicant: Rohm and Haas Company, Collegeville, PA (US)

(72) Inventors: Joseph F. Dewilde, King of Prussia, PA (US); Kirk W. Limbach, Dresher, PA (US); Reetam Chakrabarti, Phoenixville, PA (US)

(73) Assignee: ROHM AND HAAS COMPANY, Collegeville, PA (US)

( * ) Notice: Subject to any disclaimer, the term of this patent is extended or adjusted under 35 U.S.C. 154(b) by 491 days.

(21) Appl. No.: 18/254,529

(22) PCT Filed: Nov. 17, 2021

(86) PCT No.: PCT/US2021/059595

§ 371 (c)(1),
(2) Date: May 25, 2023

(87) PCT Pub. No.: WO2022/119708

PCT Pub. Date: Jun. 9, 2022

(65) Prior Publication Data

US 2024/0010592 A1 Jan. 11, 2024

Related U.S. Application Data

(60) Provisional application No. 63/119,740, filed on Dec. 1, 2020.

(51) Int. Cl.

| | |
|---|---|
| *C07C 1/04* | (2006.01) |
| *B01J 21/06* | (2006.01) |
| *B01J 23/08* | (2006.01) |
| *B01J 29/035* | (2006.01) |
| *B01J 29/70* | (2006.01) |
| *B01J 35/64* | (2024.01) |
| *C07C 11/04* | (2006.01) |
| *C07C 45/50* | (2006.01) |

(52) U.S. Cl.
CPC ............. *C07C 45/50* (2013.01); *B01J 21/066* (2013.01); *B01J 23/08* (2013.01); *B01J 29/035* (2013.01); *B01J 29/7015* (2013.01); *B01J 35/643* (2024.01)

(58) Field of Classification Search
CPC ........... C07C 1/04; C07C 45/50; C07C 11/04; C07C 11/06; B01J 39/643; B01J 21/066; B01J 23/08; C10G 2/334
See application file for complete search history.

(56) References Cited

U.S. PATENT DOCUMENTS

| | | | |
|---|---|---|---|
| 2,549,111 A | 4/1951 | Millendorf et al. | |
| 2,649,111 A | 8/1953 | Anderson | |
| 9,676,699 B2 * | 6/2017 | Limbach | ................ B01J 27/186 |
| 10,112,883 B2 | 10/2018 | Karim et al. | |
| 10,273,201 B2 | 4/2019 | Krill et al. | |
| 10,464,860 B2 | 11/2019 | Yasukawa et al. | |
| 10,513,471 B2 | 12/2019 | Nieskens et al. | |
| 10,676,419 B2 | 6/2020 | Karim et al. | |
| 10,787,611 B2 * | 9/2020 | Nieskens | ............... B01J 23/002 |
| 2010/0068773 A1 | 3/2010 | Marx et al. | |
| 2014/0206897 A1 | 7/2014 | Allman et al. | |
| 2016/0068465 A1 | 3/2016 | Allman et al. | |
| 2019/0023640 A1 | 1/2019 | Karim et al. | |

FOREIGN PATENT DOCUMENTS

| | | |
|---|---|---|
| CN | 108097286 | 6/2018 |
| CN | 108097289 | 6/2018 |
| CN | 108097290 | 6/2018 |
| CN | 108097291 | 6/2018 |
| CN | 108097305 | 6/2018 |
| CN | 109289910 A | 2/2019 |
| CN | 110743611 A | 2/2020 |
| CN | 108097324 | 3/2020 |
| CN | 108097325 | 3/2020 |
| CN | 108101767 | 9/2020 |
| CN | 108101766 | 1/2021 |
| DE | 102014112724 A1 | 3/2016 |

(Continued)

OTHER PUBLICATIONS

Ebrahimzadeh, "Alternative extractive distillation system for CO2-ethane azeotrope separation in enhanced oil recovery processes" 2016, vol. 96, p. 39-47.

(Continued)

*Primary Examiner* — Sikarl A Witherspoon

(74) *Attorney, Agent, or Firm* — CANTOR COLBURN LLP

(57) ABSTRACT

A process for preparing aldehydes from synthesis gas includes introducing a first feed stream comprising hydrogen gas and a carbon-containing gas comprising carbon monoxide into a reaction zone of a first reactor, converting the first feed stream into a first product stream comprising $C_2$ to $C_4$ hydrocarbons in the reaction zone in the presence of a first catalyst, wherein the first product stream further comprises carbon dioxide, removing water and $C_4$ and higher hydrocarbons from the first product stream to form a second feed stream, and converting the second feed stream into a second product stream comprising propionaldehyde in the presence of a second catalyst in a second reactor. The propionaldehyde can further be converted to methyl methacrylate via oxidative esterification.

16 Claims, No Drawings

(56)     References Cited

FOREIGN PATENT DOCUMENTS

| WO | 199701521 | 1/1997 |
|----|-----------|--------|
| WO | 2012063044 | 5/2012 |
| WO | 2018005074 | 1/2018 |
| WO | 2019089206 | 5/2019 |
| WO | 2020139599 | 7/2020 |

OTHER PUBLICATIONS

Nagahama, "Binary Vapor-Liquid Equilibria of Carbon Dioxide-Light Hydrocarbons at Low Temperature" 1974, vol. 7, No. 5, p. 323-328.

* cited by examiner

INTEGRATED PROCESS TO PRODUCE ALDEHYDES FROM SYNTHESIS GAS

BACKGROUND

Field

The present specification generally relates to processes that efficiently convert various carbon-containing streams to aldehydes via $C_2$ to $C_4$ hydrocarbons.

Technical Background

For a number of industrial applications, hydrocarbons are used, or are starting materials used, to produce plastics, fuels, and various downstream chemicals. $C_2$ to $C_4$ hydrocarbons are particularly useful in downstream applications, such as, for example, preparing aldehydes and further products, such as methyl methacrylate (MMA). MMA is a high-value chemical intermediate for the production of (meth)acrylic polymers and copolymers.

A variety of processes for producing lower hydrocarbons has been developed, including petroleum cracking and various synthetic processes. Synthesis gas, known as syngas, a combination of carbon monoxide and hydrogen gas, represents a flexible intermediate that can be obtained from the gasification of biomass, waste, or conventional fuels.

Synthetic processes for converting syngas to lower hydrocarbons, are known. The Fischer-Tropsch process has been used to convert syngas to a mixture of olefins along with longer chain paraffins. The Fischer-Tropsch process produces a broad product distribution and selectivity of lower olefins is typically relatively limited. To increase selectivity to lower olefins, variations of the Fischer-Tropsch process have been developed, such as the process disclosed in WO 2019/089206.

However, there are at least two azeotropes that encumber the separation in typical syngas to olefin plants, including ethylene/carbon dioxide and ethane/carbon dioxide. See Nagahama et al., *Journal of Chemical Engineering of Japan*, 7, 5, 1974, pp. 323-328. Separating the carbon dioxide from the olefins is a costly process. While extractive distillation can help break one or the other of these azeotropes, the presence of both azeotropes encourages the use of a non-distillation separation, such as amine scrubbing, of $CO_2$ in syngas to olefin operations.

Some of these processes include co-feeding $CO_2$ to the process to reduce the net $CO_2$ selectivity, determined by the $CO_2$ in the product stream less the total $CO_2$ in the feed stream, which may be negative. However, this approach typically leads to reduced productivity of the desired $C_2$ to $C_4$ hydrocarbons.

Other process, such as that disclosed in U.S. Pat. No. 10,513,471, use a special catalyst to minimize formation of $CO_2$ in a two-reactor process that converts syngas to $C_2$ to $C_5$ hydrocarbons.

U.S. Pat. No. 10,676,419 discloses a two-stage catalyst process for converting syngas to acetic acid, acrylic acid, and/or propylene. In a first stage, syngas is contacted with a first catalyst to produce a first product stream comprising $C_2$ and $C_3$ olefins and/or $C_2$ and $C_3$ paraffins, and the first product stream is then contacted with oxygen gas a second catalyst to produce acrylic acid and acetic acid.

Accordingly, a need exists for processes and systems in which aldehydes and/or methyl methacrylate can be produced from syngas efficiently and with high yield.

SUMMARY

One aspect of the present invention relates to a process comprising introducing a first feed stream comprising hydrogen gas and a carbon-containing gas comprising carbon monoxide into a reaction zone of a first reactor, converting the first feed stream into a first product stream comprising $C_2$ to $C_4$ hydrocarbons in the reaction zone in the presence of a first catalyst, wherein the first product stream further comprises carbon dioxide, removing water and $C_4$ and higher hydrocarbons from the first product stream to form a second feed stream, and converting the second feed stream into a second product stream comprising propionaldehyde and/or butyraldehyde in the presence of a second catalyst in a second reactor.

Additional features and advantages will be set forth in the detailed description which follows, and in part will be readily apparent to those skilled in the art from that description or recognized by practicing the embodiments described herein, including the detailed description which follows and the claims.

It is to be understood that both the foregoing general description and the following detailed description describe various embodiments and are intended to provide an overview or framework for understanding the nature and character of the claimed subject matter.

DETAILED DESCRIPTION

As used herein, it is noted that "synthesis gas" and "syngas" are utilized herein to represent a mixture comprising primarily hydrogen, carbon monoxide, and very often some carbon dioxide.

Reference will now be made in detail to embodiments of processes utilizing syngas to prepare $C_2$ to $C_4$ hydrocarbons and further to aldehydes and/or methyl methacrylate.

In general, in syngas to hydrocarbon processes, it is desirable to achieve a high productivity of the desired $C_2$ to $C_4$ hydrocarbons, while simultaneously reducing the net selectivity of $CO_2$. A known method to reduce the net selectivity of $CO_2$ is by co-feeding $CO_2$. However, by co-feeding additional $CO_2$ to reduce the net selectivity of $CO_2$, this also results in a decreased productivity of the desired $C_2$ to $C_4$ hydrocarbons. However, the present inventors have recognized that by directly subjecting a product stream comprising $C_2$ to $C_4$ hydrocarbons and $CO_2$ to a hydroformylation or oxo process to produce aldehydes, such as propionaldehyde, the $CO_2$ can either pass as an inert or participate in water gas shift to remake CO reactant. Further, any unreacted CO, hydrogen, and $CO_2$ can be recycled back to the syngas feed stream for more complete carbon utilization.

By eliminating the need for breaking any azeotropes formed with $CO_2$, such as, for example, ethylene/$CO_2$ or ethane/$CO_2$, significant savings can be achieved in capital and operating costs, in addition to the more complete carbon utilization that can be achieved when the $CO_2$ is recycled back to the syngas feed stream.

In the process of the present invention, a first feed stream comprising hydrogen gas and a carbon-containing gas comprising carbon monoxide is introduced into a reaction zone of a first reactor. Preferably, the first feed stream comprises syngas. The syngas may comprise hydrogen and carbon monoxide, which may optionally be supplemented with carbon dioxide depending on the level of carbon dioxide, if any, present in the syngas.

The hydrogen may present in the first feed stream in an amount of from 10.0 vol % to vol % H2, such as from 20.0 vol % to 80.0 vol % H2 or from 30.0 vol % to 70.0 vol % H2 based on the total volume of the first feed stream.

The carbon dioxide may be present in the first feed stream in an amount of from 0 vol % to 20.0 vol % CO2 relative to the total volume of the first feed stream. Any carbon dioxide present in the feed stream may be present in the syngas or recycled back to the first feed stream from the second product stream. Fresh carbon dioxide, e.g., a carbon dioxide co-feed, does not need to be added to the first feed stream as the downstream process may use carbon dioxide generated in the first reactor.

The first feed stream may have an CO2/CO volume ratio from 0 to 1.50, such as from 0.05 to 1.50, from 0.25 to 1.50, or from 0.50 to 1.50. Preferably, the ratio of CO2/CO is high enough that there is sufficient CO2 to convert carbon to C2 to C4 hydrocarbons.

The first catalyst may comprise any known catalyst for converting a syngas to C2 to C4 hydrocarbons. For example, the first catalyst may comprise a mixed metal oxide catalyst or a bifunctional or hybrid catalyst comprising a mixed metal oxide catalyst and a microporous catalyst component, such as, for example, a zeolite component.

The mixed metal oxide catalyst component may be a bulk catalyst or a supported catalyst and may be made by any suitable method, such as co-precipitation, impregnation, or the like. The mixed metal oxide catalyst may comprise, for example, cobalt (Co), manganese (Mn), copper (Cu), zinc (Zn), chromium (Cr), aluminum (Al), gallium (Ga), zirconium (Zr), and combinations thereof. It should be understood that any metal in the mixed metal oxide component mixture can be present in a variety of oxidation states. It should also be understood that the designation of a specific oxide (e.g. Ga2O3), does not necessarily preclude the presence of an additional or different oxide of the given metal(s).

A hybrid catalyst systems comprise a mixed metal oxide catalyst component, which converts the first feed stream oxygenated hydrocarbons, and a microporous catalyst component (such as, for example, a zeolite component), which converts the oxygenates to hydrocarbons. The microporous catalyst component may be selected from molecular sieves having 8-MR pore access and having a framework type selected from the group consisting of the following framework types CHA, AEI, AFX, ERI, LTA, UFI, RTH, RHO, LEV, and combinations thereof, the framework types corresponding to the naming convention of the International Zeolite Association. It should be understood that both aluminosilicate and silicoaluminophosphate frameworks may be used. Preferably, the molecular sieve has a Chabazite (CHA) framework type. For example, the molecular sieve may be SAPO-34 silicoaluminophosphate having a Chabazite (CHA) framework type.

Examples of these may include, but are not necessarily limited to: CHA embodiments selected from SAPO-34 and SSZ-13; and AEI embodiments such as SAPO-18. Combinations of microporous catalyst components having any of the above framework types may also be employed. It should be understood that the microporous catalyst component may have a different membered ring pore opening depending on the desired product. For instance, microporous catalyst component having 8-MR to 12-MR pore openings could be used depending on the desired product. However, to produce C2 to C4 hydrocarbons, a microporous catalyst component having 8-MR pore openings is preferably used.

The mixed metal oxide catalyst component and the microporous catalyst component of the hybrid catalyst may be mixed together by any suitable means, such as, for example, by physical mixing—such as shaking, stirring, or other agitation. Alternatively, the mixed metal oxide catalyst component and the microporous catalyst component may be present as a single formulated catalyst. The mixed metal oxide catalyst component and the microporous catalyst component may be present in the reaction zone, typically as a hybrid catalyst in a catalyst bed, in a weight/weight (wt/wt) ratio (mixed metal oxide catalyst component:microporous catalyst component) ranging from 0.1:1 to 10:1, such as from 0.5:1 to 9:1.

The mixed metal oxide catalyst component may be reduced within the reactor prior to exposure to the first feed stream by exposing the mixed metal oxide catalyst component to conventional reducing gases. Alternatively, the mixed metal oxide catalyst component may be reduced within the reactor upon exposure to reducing gases in the feed stream such as H2 and CO.

The reaction conditions within the reaction zone of the first reactor will now be described. The first feed stream are contacted with the first catalyst in the reaction zone of the first reactor under reaction conditions sufficient to form a first product stream comprising C2 to C4 hydrocarbons. The first product stream may further comprise higher hydrocarbons, i.e., C5 or higher hydrocarbons. Preferably, the first product stream comprises primarily C2 to C4 hydrocarbons, such as C2 to C4 olefins. More preferably, the hydrocarbons in the first product stream consists essentially of C2 to C4 olefins. As used herein, "consists essentially of C2 to C4 olefins" means the first product stream comprises at least 70 vol % C2 to C4 olefins based on the total volume of hydrocarbons in the first product stream. The reaction conditions comprise a temperature within the reaction zone ranging, for example, from 300° C. to 500° C., such as from 380° C. to 450° C., from 380° C. to 440° C., from 380° C. to 430° C., from 380° C. to 420° C., from 380° C. to 410° C., from 380° C. to 400° C., or from 380° C. to 390° C.

The reaction conditions also include, for example, a pressure inside the reaction zone of at least 20 bar (20,000 kilopascals (kPa)), such as at least 25 bar (25,000 kPa), at least 30 bar (30,000 kPa), at least 35 bar (35.00 kPa), at least 40 bar (40,000 kPa), at least 45 bar (45,000 kPa), at least 50 bar (50,000 kPa), at least 55 bar (55,000 kPa), at least 60 bar (60,000 kPa), at least 65 bar (65,000 kPa), or at least 70 bar (70,000 kPa).

The reaction conditions also include, for example, a gas hourly space velocity inside the reaction zone 101 of at least 2500 hr-1, such as at least 3000 hr-1, such as at least 3600 hr-1, such as at least 4200 hr-1, such as at least 4800 hr-1, such as at least 5400 hr-1, such as at least 6000 hr-1, such as at least 6600 hr-1, or such as at least 7200 hr-1.

The first product stream comprises C2 to C4 hydrocarbons and further comprises carbon dioxide. The carbon dioxide present in the first product stream is not removed from the product stream. The first product stream may also contain unreacted carbon monoxide and hydrogen, as well as C2 to C4 paraffins.

Water is removed from the first product stream. Additionally C4 and higher hydrocarbons are also removed from the first product stream to form a second feed stream, which is fed to the second reactor. Depending on the desired aldehydes, C3 hydrocarbons can be removed with the C4 and higher hydrocarbons. Alternatively, the C3 hydrocarbons can be sent in the overhead stream as part of the second feed stream for conversion to butyraldehyde in the hydroformylation or oxo process in the second reactor. Butyraldehyde can be used to make n-butanol or 2-ethylhexanol. Catalysts for this process include, but are not limited to, (organo) phosphines, phosphites, or bidentate ligand complexes comprising Group VIII and VIIIB metals.

The second feed stream comprises C2 hydrocarbons and optionally the C3 hydrocarbons, as well as carbon dioxide and unreacted hydrogen and carbon monoxide. The second feed stream is converted into a second product stream in the presence of a second catalyst in a second reactor. The second feed stream is subjected to a hydroformylation reaction or oxo process in the second reactor to form aldehydes from the hydrocarbons present in the second feed stream. If the C3 hydrocarbons are removed from the first product stream with the higher hydrocarbons, the primary product of the second reactor is propionaldehyde. When the C3 hydrocarbons are not removed from the first product stream, the product of the second reactor primarily comprises a mixture of propionaldehyde and butyraldehyde. The carbon dioxide present in the second feed stream either passes through the second reactor as an inert material or participates in water gas shift to form carbon monoxide.

The second product stream comprises the produced aldehydes and may also comprise paraffins. The second product stream further comprises carbon dioxide and any unreacted hydrogen and carbon monoxide. The aldehyde products may be separated from the second product stream and an additional separation may remove any paraffins from the remaining carbon dioxide, carbon monoxide and hydrogen. Preferably, the carbon dioxide, carbon monoxide and hydrogen is recycled to the first reactor and is combined with the first feed stream entering the first reactor.

Propionaldehyde from the second product stream may be further reacted to form methyl methacrylate via an oxidative esterification reaction using any known method. For example, propionaldehyde can be converted to methacrolein in the presence of formaldehyde. The methacrolein can subsequently be converted to methyl methacrylate.

It will be apparent to those skilled in the art that various modifications and variations can be made to the embodiments described herein without departing from the spirit and scope of the claimed subject matter. Thus, it is intended that the specification cover the modifications and variations of the various embodiments described herein provided such modification and variations come within the scope of the appended claims and their equivalents.

What is claimed is:

1. A process comprising:

introducing a first feed stream comprising hydrogen gas and a carbon-containing gas comprising carbon dioxide and carbon monoxide into a reaction zone of a first reactor, wherein a volume ratio of carbon dioxide to carbon monoxide in the feed stream is from 0.25 to 1.5;

converting the first feed stream into a first product stream comprising $C_2$ to $C_4$ hydrocarbons in the reaction zone in the presence of a first catalyst, wherein the first product stream further comprises carbon dioxide;

removing water and $C_4$ and higher hydrocarbons from the first product stream to form a second feed stream;

converting the second feed stream into a second product stream comprising propionaldehyde in the presence of a second catalyst in a second reactor.

2. The process of claim 1, wherein the carbon dioxide from the first product stream exiting the second reactor is recycled to the first feed stream.

3. The process of claim 1, further comprising recycling unreacted hydrogen and carbon monoxide to the first feed stream.

4. The process of claim 1, wherein the second product stream further comprises butyraldehyde.

5. The process of claim 1, wherein the step of removing water and $C_4$ hydrocarbons from the first product stream further comprises removing $C_3$ hydrocarbons from the first product stream.

6. The process of claim 1, further comprising removing the propionaldehyde from the second product stream.

7. The process of claim 1, further comprising removing any paraffins from the second product stream.

8. The process of claim 1, further comprising converting the propionaldehyde to methyl methacrylate via oxidative esterification.

9. The process of claim 1, wherein the reaction zone operates at a pressure of at least 20 bar.

10. The process of claim 1 wherein the first catalyst comprises a mixed metal oxide catalyst or comprises a hybrid catalyst comprising a mixed metal oxide catalyst and a microporous catalyst component.

11. The process of claim 10, wherein the mixed metal oxide catalyst component comprises $ZrO_2$.

12. The process of claim 10, wherein the mixed metal oxide catalyst component comprises $ZrO_2$ and $Ga_2O_3$.

13. The process of claim 10, wherein the microporous catalyst component is a molecular sieve having 8-MR pore openings.

14. The process of claim 10, wherein the microporous catalyst component is a molecular sieve having a Chabazite (CHA) framework.

15. The process of claim 10, wherein the microporous catalyst component is SAPO-34.

16. The process of claim 1, wherein the $C_2$ to $C_4$ hydrocarbons consist essentially of $C_2$ to $C_4$ olefins.

* * * * *